United States Patent [19]

Ohsaka et al.

[11] 4,264,530
[45] Apr. 28, 1981

[54] PROCESS FOR PREPARING HIGH PURITY TETRAFLUOROMETHANE

[75] Inventors: Yohnosuki Ohsaka; Heikitsu Sonoyama, both of Osaka, Japan

[73] Assignee: Daikin Kogyo Co., Ltd., Osaka, Japan

[21] Appl. No.: 124,271

[22] Filed: Feb. 25, 1980

[30] Foreign Application Priority Data

Feb. 26, 1979 [JP] Japan .................................. 54-22218

[51] Int. Cl.$^3$ ............................................. C07C 19/08
[52] U.S. Cl. .................................................... 570/166
[58] Field of Search ...................................... 260/653.7

[56] References Cited

U.S. PATENT DOCUMENTS 2,745,886  5/1956  Ruh et al. ........................... 260/653.7
3,258,500  6/1966  Swamer et al. .................... 260/653.7

Primary Examiner—Delbert E. Gantz
Assistant Examiner—Joseph A. Boska
Attorney, Agent, or Firm—Birch, Stewart, Kolasch and Birch

[57] ABSTRACT

A process for preparing high purity tetrafluoromethane which comprises the steps of (a) passing a gaseous mixture of chlorotrifluoromethane and hydrogen fluoride in a molar proportion of 1:1 to 1:10 through a catalyst layer of chromium oxyfluoride at a temperature of 380° to 420° C. under a pressure of 1 to 5 atm with a space velocity of 10 to 150 hr$^{-1}$, (b) washing the gaseous reaction mixture obtained in the foregoing step (a) with water or an aqueous alkaline solution so as to remove acidic materials therefrom, (c) passing the resultant gaseous mixture with hydrogen fluoride in an amount of 0.2 to 10 mole to 1 mole of the combined amount of chlorotrifluoromethane and tetrafluoromethane in the gaseous mixture through a catalyst layer of chromium oxyfluoride at a temperature of 380° to 420° C. under a pressure of 1 to 5 atm with a space velocity of 10 to 300 hr$^{-1}$ and (d) washing the gaseous reaction mixture obtained in the foregoing step (c) with water or an aqueous alkaline solution so as to remove acidic materials therefrom, optionally followed by effecting the same operations as in the latter two steps repeatedly one or more times until a desired purity of tetrafluoromethane is obtained.

6 Claims, No Drawings

PROCESS FOR PREPARING HIGH PURITY TETRAFLUOROMETHANE

This invention relates to a process for preparing high purity tetrafluoromethane.

Tetrafluoromethane is used in dry etching (i.e. plasma etching) of silicon semiconductors and is required to be highly pure.

For preparation of tetrafluoromethane, there are known various processes including a process comprising reacting chlorotrifluoromethane with hydrogen fluoride in the presence of a catalyst, a process comprising reacting trifluoromethane with fluorine and a process comprising pyrolyzing tetrafluoroethylene into tetrafluoromethane and carbon. Among them, the process using trifluoromethane as the starting material requires fluorine gas so that it is expensive and dangerous. The process using tetrafluoroethylene as the starting material can hardly be carried out continuously and safely since the reaction in the process proceeds with violence. In contrast, the process using chlorotrifluoromethane as the starting material is advantageous since it uses inexpensive hydrogen fluoride as a source of fluorine and the reaction therein can proceed continuously and safely. However, tetrafluoromethane prepared by this process inevitably contains unreacted chlorotrifluoromethane, the removal of which from the reaction product is extremely difficult. For example, when chlorotrifluoromethane and hydrogen fluoride are reacted in the presence of chromium oxyfluoride under such conditions as favorable to fluorination (temperature, 400° C.; molar ratio of hydrogen fluoride and chlorotrifluoromethane, 20:1; specific velocity, 40 hr$^{-1}$), the obtained tetrafluoromethane contains chlorotrifluoromethane in a concentration of 200 ppm by mole. Noticeably, this result is obtained under the uneconomical condition in which hydrogen fluoride is used in extremely large excess.

Furthermore, tetrafluoromethane produced in any of the above mentioned processes is purified by distillation. It requires an expensive apparatus resistant to a high pressure and a dangerous operation since tetrafluoromethane has a critical temperature of −45.7° C. and a critical pressure of 38.2 atm.

A main object of the present invention is to make it possible to produce high purity tetrafluoromethane not requiring an extremely large excess amount of hydrogen fluoride and an expensive apparatus without any dangerous operation. This object can be achieved by contacting a gaseous mixture of chlorotrifluoromethane and hydrogen fluoride with chromium oxyfluoride, removing acidic materials from the resultant gaseous mixture, contacting the gaseous mixture after removal of the acidic materials with hydrogen fluoride on chromium oxyfluoride and removing acidic materials from the resulting gaseous mixture, if necessary, with repetition of the last two operations one or more times. By the above process, the chlorotrifluoromethane content in tetrafluoromethane can be decreased below 20 ppm by mole without using a large excess amount of hydrogen fluoride or requiring any expensive apparatus as well as any dangerous operation.

The process of the invention comprises at least four steps or operations, i.e. the first step for reacting chlorotrifluoromethane with hydrogen fluoride in the presence of chromium oxyfluoride, the second step for removing acidic materials from the gaseous reaction mixture obtained in the first step, the third step for reacting chlorotrifluoromethane remained in the gaseous mixture from the second step with hydrogen fluoride in the presence of chromium oxyfluoride and the fourth step for removing acidic materials from the gaseous reaction mixture obtained in the third step.

In the first step, the reaction is usually carried out by passing a mixture of chlorotrifluoromethane with hydrogen fluoride through a reactor packed with chromium oxyfluoride at a temperature of from 380° to 420° C. When the temperature is lower than 380° C., the reaction rate is considerably lower, and in order to achieve an industrially advantageous conversion, it is necessary to perform the reaction with a low space velocity. This requires a reactor of large capacity. When the reaction temperature is higher than 420° C., the catalyst is extremely deteriorated. Thus, such high temperature does not suit for the industrial production. The reaction pressure is not particularly limited. Preferred is a pressure from 1 to 5 atm. The space velocity is preferably from 10 to 150 hr$^{-1}$. The space velocity depends on the reaction temperature. A smaller space velocity results in a higher conversion. However, when the space velocity is smaller than 10 hr$^{-1}$, no further increase in the conversion is obtained. On the other hand, when the space velocity is larger than 150 hr$^{-1}$, the conversion is much decreased.

The molar ratio of hydrogen fluoride and chlorotrifluoromethane may be from 1:1 to 10:1. With the increase of the proportion of hydrogen fluoride, the proportion of chlorotrifluoromethane to tetrafluoromethane in the reaction product decreases. Too large excess use of hydrogen fluoride results in the loss of hydrogen fluoride since it is removed together with hydrogen chloride as an acidic material in the subsequent washing step. When the proportion of hydrogen fluoride is lower than the said lower limit, the satisfactory conversion of chlorotrifluoromethane to tetrafluoromethane is not achieved. The most preferable molar ratio of hydrogen fluoride and chlorotrifluoromethane is from 2:1 to 8:1.

In the second step, the removal of acidic materials from the gaseous mixture from the foregoing step is carried out effectively by passing it through water and then through an aqueous alkaline solution. The resulting gaseous product is preferably dried over a drying agent such as calcium chloride.

The gaseous product after removal of acidic materials in the second step comprises a large amount of tetrafluoromethane and a small amount of chlorotrifluoromethane. This gaseous product is then introduced together with hydrogen fluoride into a reactor where chromium oxyfluoride is packed. The amount of hydrogen fluoride to be used may be from 0.2 to 10 mole per 1 mole of the combined amount of tetrafluoromethane and chlorotrifluoromethane in the gaseous product. With increase of the amount of hydrogen fluoride, the chlorotrifluoromethane content in the produced tetrafluoromethane will be decreased. However, the amount of hydrogen fluoride is larger than the higher limit, the amount of unreacted hydrogen fluoride is increased, and this is not economical. When the amount of hydrogen fluoride is smaller than the said lower limit, the conversion of chlorotrifluoromethane to tetrafluoromethane is not satisfactory. The most preferable amount of hydrogen fluoride is from 0.3 to 5 mole per 1 mole of the combined amount of tetrafluoromethane and chlorotrifluoromethane.

Thus, in the third step, the reaction is preferably carried out at a temperature of from 380° to 420° C. When the temperature is lower than 380° C., the reaction rate is so low that the chlorotrifluoromethane content in the obtained tetrafluoromethane will not be sufficiently low. When it is higher than 420° C., the catalyst is extremely deteriorated. Thus, such high temperature is not suitable for industrial production. The reaction pressure is not particularly limited. Preferred is a pressure from 1 to 5 atm. The space velocity may vary with the reaction temperature and the desired content of chlorotrifluoromethane in the final product. Preferable space velocity is from 1 to 300 hr$^{-1}$.

In the fourth step, the removal of acidic materials from the gaseous reaction mixture obtained in the foregoing step is effected by passing it through water and an aqueous alkaline solution in order. The resultant gaseous product is preferably dried over a drying agent such as calcium chloride.

The thus obtained gaseous product almost or substantially consists of tetrafluoromethane. When desired, however, the same operations as in the said third and fourth steps may be applied repeatedly one or more times so as to increase the purity of tetrafluoromethane.

For carrying out advantageously the reaction with hydrogen fluoride in the presence of chromium oxyfluoride in the third or any later step, it is desirable to make the proportion of chlorotrifluoromethane to tetrafluoromethane in the gaseous reaction mixture obtained in the first step below 10 mole %, preferably below 1 mole %.

Chromium oxyfluoride is a known catalyst for fluorination comprising chromium bonded with oxygen and fluorine and prepared, for example, by heating chromium (III) hydroxide in the presence of hydrogen fluoride at a temperature of from 200° to 600° C. or by heating chromium fluoride hydrate (e.g. $CrF_3 \cdot 3H_2O$) in the presence of oxygen at a temperature of from 350° to 750° C. (cf. Japanese Patent Publication No. 10601/1968 and U.S. Pat. No. 2,745,886).

The present invention will be hereinafter explained in detail by the following Examples.

REFERENCE EXAMPLES 1 TO 7

Into a Hastelloy C made tubular reactor of 1.5 inch in diameter sustained vertically in an electric furnace, chromium oxyfluoride pellets (each having a diameter of 4 mm and a length of 6 mm; 300 ml) obtained by heating $CrF_3 \cdot 3H_2O$ in an oxygen stream at 500° C. were charged, and the temperature was raised up to a designed one. Chlorotrifluoromethane and hydrogen fluoride in a designed molar ratio were fed into the reactor from its top with a space velocity as designed. The reaction was carried out under atmospheric pressure.

The gaseous reaction mixture discharged from the reactor was washed with water and an aqueous alkaline solution in order, dried over calcium chloride and collected in a trap cooled with liquid oxygen. The gas just before trapped was subjected to gas chromatographic analysis. The results are shown in Table 1.

From the results thus obtained, it is understood that tetrafluoromethane produced in one step reaction contains chlorotrifluoromethane in a concentration of several hundred ppm even when the reaction is performed at a high temperature and at a small space velocity with a high proportion of hydrogen fluoride to tetratrifluoromethane.

TABLE 1

| Reference Example | Reaction conditions ||| Discharged gas composition (% by mole) |||
|---|---|---|---|---|---|---|
| | Temp. (°C.) | HF/CClF$_3$ (mole/mole) | Space velocity (hr$^{-1}$) | CF$_4$ | CClF$_3$ | CCl$_2$F$_2$ |
| 1 | 380 | 2.6 | 40 | 91.8 | 8.15 | 0.02 |
| 2 | 400 | 2.6 | 150 | 91.0 | 9.0 | 0.01 |
| 3 | 400 | 2.6 | 40 | 99.0 | 0.84 | 0.00 |
| 4 | 400 | 4.0 | 40 | 99.9 | 0.06 | 0.00 |
| 5 | 400 | 4.0 | 10 | 99.9 | 0.06 | 0.00 |
| 6 | 400 | 20 | 40 | 99.9 | 0.02 | 0.00 |
| 7 | 420 | 2.6 | 40 | 99.7 | 0.25 | 0.00 |

EXAMPLES 1 TO 4

Two series of the system comprising a reactor in an electric furnace, a water washing tower, an aqueous alkaline solution washing tower and a calcium chloride drying tower were arranged successively. To an inlet of the reactor in the second system, a hydrogen fluoride supply pipe was connected, and a trap cooled with liquid oxygen was provided next to the calcium chloride drying tower.

In the reactor of the first system, the reaction was carried out under the conditions of Reference Example 3 or 4. In the reactor of the second system, the reaction was performed under atmospheric pressure with the conditions as shown in Table 2.

The gas chromatographic analysis of the gas just before trapped gave the results as shown in Table 2.

TABLE 2

| Example | Reaction condition in the 1st system | Reaction condition in the 2nd system ||| CClF$_3$ in discharged gas (ppm by mole) |
|---|---|---|---|---|---|
| | | Temp. (°C.) | HF/CClF$_3$ introduced in the 1st system (mole/mole) | Calculated space velocity (hr$^{-1}$) | |
| 1 | Reference Example 3 | 400 | 2.6 | 40 | 11 |
| 2 | Reference Example 4 | 400 | 3 | 36 | 0.8 |
| 3 | Reference Example 4 | 400 | 1 | 16 | 2 |
| 4 | Reference Example 4 | 420 | 1 | 16 | 1.5 |

EXAMPLE 5

Into a Hastelloy C made, tubular reactor of 1.5 inch in diameter sustained vertically in an electric furnace, chromium oxyfluoride pellets (each having a diameter of 4 mm and a length of 6 mm; 300 ml) obtained by heating chromium hydroxide in a hydrogen fluoride stream at 450° C. were charged. To the reactor, a water washing tower, an aqueous alkaline solution washing tower and a calcium chloride drying tower were successively connected to construct the first system. To the first system, the second system having the same construction as above was connected, and a trap cooled with liquid oxygen was provided at the end. Further, a hydrogen fluoride supply pipe was connected to the inlet of the reactor in the second system.

Hydrogen fluoride and chlorotrifluoromethane in a molar ratio of 4:1 were passed through the reactor of the first system at 400° C. with a space velocity of 40 hr$^{-1}$. The gas discharged from the first system was combined with hydrogen fluoride in an amount of 1 mole to 1 mole of the combined amount of chlorotrifluoromethane and tetrafluoromethane in the said gas and passed through the reactor of the second system at 400° C. with a space velocity of 16 hr$^{-1}$ (calculated) to obtain tetrafluoromethane of high purity. The gas chromatographic analysis of the gas just before trapped showed that the obtained tetrafluoromethane contains only 2 ppm by mole of chlorotrifluoromethane.

What is claimed is:

1. A process for preparing high purity tetrafluoromethane which comprises the steps of (a) passing a gaseous mixture of chlorotrifluoromethane and hydrogen fluoride through a catalyst layer of chromium oxyfluoride, (b) removing acidic materials from the gaseous reaction mixture obtained in the foregoing step (a), (c) passing the resultant gaseous mixture with hydrogen fluoride through a catalyst layer of chromium oxyfluoride and (d) removing acidic materials from the gaseous reaction mixture obtained in the foregoing step (c).

2. The process according to claim 1, wherein the molar proportion of chlorotrifluoromethane and hydrogen fluoride to be passed through the catalyst layer in the step (a) is from 1:1 to 1:10.

3. The process according to claim 2, wherein the passing in the step (a) is carried out at a temperature of 380° to 420° C. under a pressure of 1 to 5 atm with a space velocity of 10 to 150 hr$^{-1}$.

4. The process according to claim 1, 2 or 3, wherein the amount of hydrogen fluoride to be admixed with the gaseous mixture to be passed through the catalyst layer in the step (c) is from 0.2 to 10 mole to 1 mole of the combined amount of chlorotrifluoromethane and tetrafluoromethane in the gaseous mixture.

5. The process according to claim 4, wherein the passing in the step (c) is carried out at a temperature of 380° to 420° C. under a pressure of 1 to 5 atm with a space velocity of 10 to 300 hr$^{-1}$.

6. A process according to claim 1, and further comprising effecting the same operations of steps (c) and (d) repeatedly, one or more times, until a desired purity of tetrafluoromethane is obtained.

* * * * *